United States Patent
Li et al.

(10) Patent No.: US 8,237,924 B2
(45) Date of Patent: Aug. 7, 2012

(54) LONG OPTICAL PATH GAS MONITOR

(75) Inventors: Hongjie Li, Hubei (CN); Xinfeng Fan, Hubei (CN)

(73) Assignee: Wuhan Tianhong Instruments Co., Ltd., Hubei (CN)

( * ) Notice: Subject to any disclaimer, the term of this patent is extended or adjusted under 35 U.S.C. 154(b) by 320 days.

(21) Appl. No.: 12/673,255

(22) PCT Filed: Jun. 20, 2008

(86) PCT No.: PCT/CN2008/071399
§ 371 (c)(1),
(2), (4) Date: Feb. 12, 2010

(87) PCT Pub. No.: WO2009/021420
PCT Pub. Date: Feb. 19, 2009

(65) Prior Publication Data
US 2011/0194108 A1    Aug. 11, 2011

(30) Foreign Application Priority Data
Aug. 15, 2007 (CN) .......................... 2007 1 0142535

(51) Int. Cl.
*G01J 3/28* (2006.01)
(52) U.S. Cl. ..................................................... 356/326
(58) Field of Classification Search .................. 356/326, 356/328, 330, 334
See application file for complete search history.

(56) References Cited

U.S. PATENT DOCUMENTS

| 4,060,326 A | 11/1977 | Tirabassi et al. |
| 4,891,518 A * | 1/1990 | Day .......................... 250/339.13 |
| 5,892,618 A * | 4/1999 | Filas ............................. 359/360 |
| 6,747,736 B2 * | 6/2004 | Takahashi ..................... 356/319 |

FOREIGN PATENT DOCUMENTS
CN     2494988     6/2002

OTHER PUBLICATIONS

Wu et al.; "Long-path Differential Optical Absorption Spectroscopy for Air Pollution Monitoring".

* cited by examiner

*Primary Examiner* — Tarifur Chowdhury
*Assistant Examiner* — Abdullahi Nur
(74) *Attorney, Agent, or Firm* — Chun-Ming Shih; HDLS IPR Services

(57) ABSTRACT

A long optical path gas monitor is open-typed or close-typed. The monitor includes an optical generation part and a signal processing part. Said optical generation part comprises an emitter, a receiver and multi-group concave mirrors or prisms used to form enough optical path between the emitter and the receiver. Said signal processing part includes an optical fiber (21), a spectrometer (22), a scanner (23), an optoelectronic detector (24) and a computer (25), which are connected sequentially. The input end of the optical fiber (21) is connected to the receiver.

10 Claims, 3 Drawing Sheets

LONG OPTICAL PATH GAS MONITOR

FIELD OF THE INVENTION

The present invention relates to an environment testing technique, and more particularly to a gas analysis instrument which tests the component and content of atmospheric gas.

BACKGROUND OF THE INVENTION

For long path DOAS (Differential Optical Absorption Spectroscopy) technique, it mainly performs qualitative and quantitative analysis about the kind and concentration of trace pollution gas components in the air, based on the absorption features of trace pollution components in the air to the ultraviolet and visible wave band. The technique can monitor a plurality of trace gas components simultaneously with a measurement range from 100 meters to several thousand meters and a high sensitivity.

Generally, as for the application of long path DOAS technique, an emitter installed on a high building is used to generate light ray radiation, then the light ray is collimated and transferred to the atmospheric path through a telescope system; and at the other end (50~200 meters), a corner reflection mirror is installed for reflecting the light ray back. The light ray reflected through atmospheric path is processed by a spectrometer, then the obtained radiation spectrum is compared with lamp spectrum to get a difference between them to determine the gas components in the atmosphere. Since each kind of gas has its own characteristic absorption spectrum, the kind and concentration of the absorption gas can be determined through the analysis of the variety of spectrum.

However, the following disadvantages do exist when the long optical path gas monitor is used to monitor the gas concentration in the air: the first problem is how to select the locations of the long optical path atmospheric test monitor and installation of the same is also difficult. During the installation, the emitter must be installed at a selected location on a high building, then about 100 meters apart, another location must be selected for the receiver, there being no obstacles between the two selected locations. However, usually after a period of the installation and utilization of the monitor, new obstacles might be generated between the two selected locations, which will bring the problem of re-selection of the two locations.

Next, such remote locations selection is disadvantageous for the maintenance of the long optical path atmospheric test instrument, which needs more work and hours, so the efficiency thereof is low.

In order to overcome the above mentioned drawbacks, the inventor of the present invention, after long period of study and test, finished the present invention.

SUMMARY OF THE INVENTION

The main objective of the present invention is to provide a long optical path gas monitor to overcome the above drawbacks.

In order to achieve the above objective, the technical solution adopted in the present invention provides firstly a long optical path gas monitor which is open-typed and includes an optical generation part and a signal processing part. The optical generation part comprises: an emitter, a first planar reflection mirror installed in the optical path of the light ray emitted by the emitter, a first concave mirror installed in the optical path of the light ray reflected by the first planar mirror, a second concave mirror installed in the optical path of the light ray reflected by the first concave mirror, a third concave mirror installed in the optical path of the light ray reflected by the second concave mirror, then a fourth concave mirror installed in the optical path of the light ray reflected by the third concave mirror, and a receiver installed on the optical path of the light ray reflected by the fourth concave mirror.

The signal processing part comprises sequentially connected an optical fiber, an optical spectrometer, a scanner, an optoelectronic detector and a computer, and the input end and the receiver is connected to optical fiber.

Preferably, the monitor further includes a position adjustment unit that comprises an optical support, a rotary mechanism and a dynamic device. The optical generation part is installed on the optical support. The output end of the rotary mechanism is connected and fixed to the optical support to make the optical support rotate. The input end of the rotary mechanism is connected to the input end of the dynamic device so as to provide power to the rotary mechanism.

Preferably, the optical generation part is divided into a first optical component which is composed of the first concave mirror and the third concave mirror, and a second optical component which is composed of the emitter, the second concave mirror, the fourth concave mirror and the emitter. The first optical component and the second optical component are installed respectively at one of the two ends of the optical support, and the distance between the first optical component and the second optical component is in the range of 0.3 meter to 20 meters.

Preferably, the rotary mechanism includes: a rotary shaft, a bearing and a gear transmission mechanism. The gear transmission mechanism comprises a driving gear and a driven gear, the driven gear is fixed on the rotary shaft and is meshed with the driving gear. The bearing is capped to the rotational shaft, and the input end of the rotary mechanism acts as the output end of the rotary shaft.

Preferably, the monitor further includes a gearbox. The output shaft of the gearbox is connected to the driving gear, and the input end of the gearbox is connected to the output end of the power device.

Preferably, the monitor further includes an anemoscope connected to the computer, the computer is connected to the control end of the power device, and wherein the power device is a motor.

Preferably, the monitor further includes a first lens which is installed between the emitter and the first planar reflection mirror.

Preferably, the radius of curvature of the first concave mirror, the second concave mirror, the third concave mirror and the fourth concave mirror is in the range of 20 cm to 500 cm;

Preferably, the material of the first planar reflection mirror and all the concave mirrors is silica or ultraviolet optical fused silica of which the reflecting surface coated with Au or Ag and a protection film is also coated.

Next, there provided a long optical path gas monitor, which is closed-typed and includes an optical generation part and a signal processing part, wherein the optical generation part is installed within a closed body with an inlet and an outlet of tested gas.

The optical generation part comprises: an emitter which is located outside of the closed body, a plurality of prisms which are installed correspondingly on the side walls of the closed body, wherein, a first prism receives the light ray emitted by the emitter, a second prism is set at the optical path through the first prism, a third prism is set at the optical path of total reflection by the second prism, a fourth prism is set at the optical path of total reflection by the third prism, then until a $2k_{th}$ prism is set up at the optical path of total reflection by a $(2k-1)_{th}$ prism; and an optoelectronic receiver installed at the external side of the closed body to receive the optical light ray passed through the $2k_{th}$ prism, wherein k is a natural number and is larger than or equal to 2;

The signal processing part includes an optical fiber, a spectrometer, a scanner, an optoelectronic detector and a processor, which are sequentially connected, the input end of the optical fiber being connected to the optoelectronic receiver.

Preferably, a clean air curtain is installed in the closed body.

Compared with the prior art, the present invention has the following advantages: an integrated optical system according to the present invention is used to replace the original two discrete optical systems so that the lifetime of the entire system of the present invention is greatly enhanced, a computer is used to control the rotation of the present system so that the measurement results are more accurate.

Since integrated design is adopted in the present optical system, the influence from light to the surrounding environment in the traditional optical system is overcome. From the aspect of utilization and maintenance, since the installation is only done at one position, which makes it possible to calibrate, and so adjustment is simplified and maintenance becomes very convenient.

With the above techniques, the present invention, which features a simple structure, a long lifetime, and a high detection accuracy, can be used in on-line detection.

DETAILED DESCRIPTION OF THE PREFERRED EMBODIMENTS

In the followings, with reference to the drawings, the above and additional technical features and advantages of the current invention will be described in more details.

Figure 1:
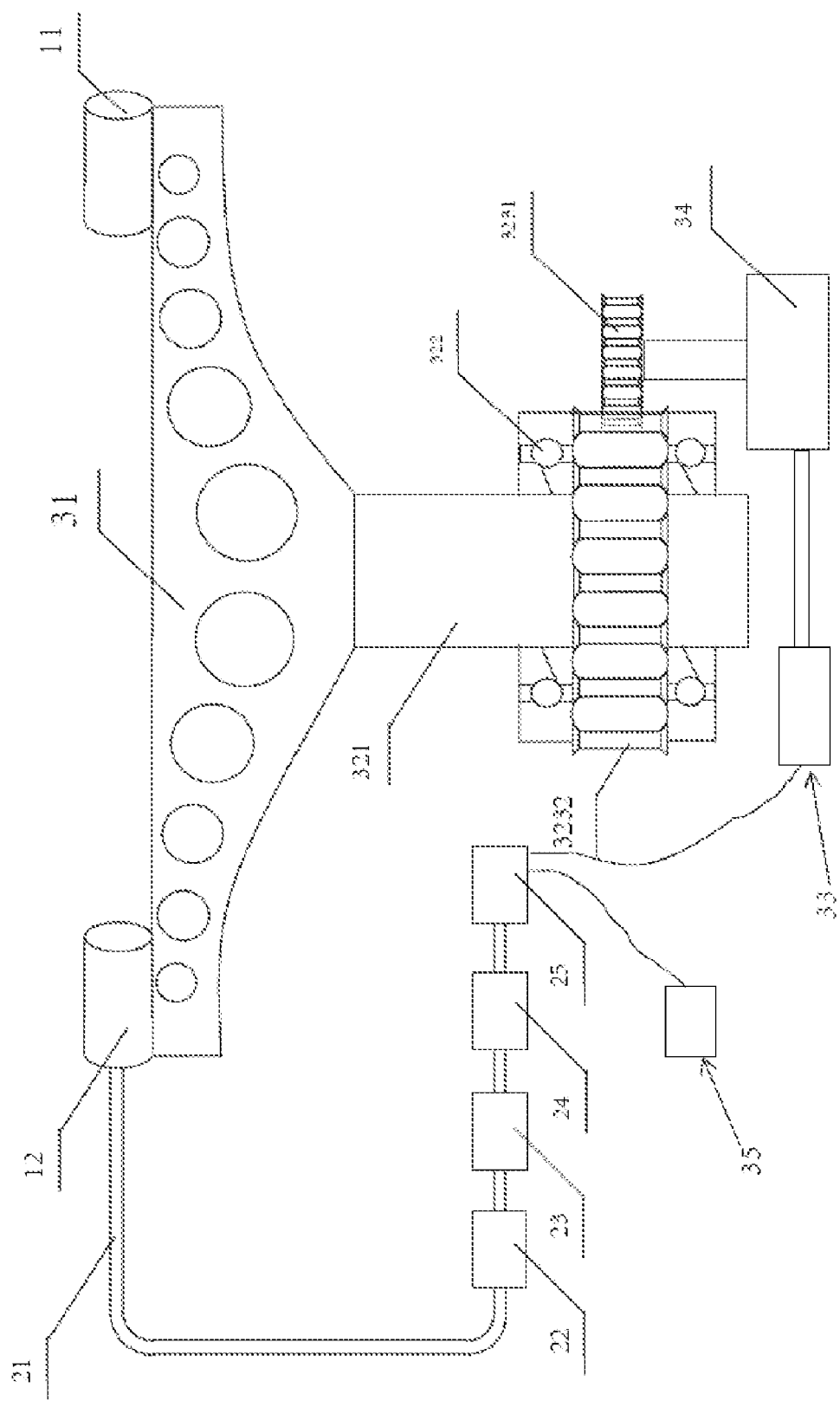
FIG. 1 is a brief structural drawing of the long optical path gas monitor according to preferred embodiment 1 of the present invention.

In FIG. 1, a brief structural drawing of the long optical path gas monitor according to preferred embodiment 1 of the present invention is shown. The monitor includes an optical generation part and a signal processing part. The optical generation part is used to generate sufficient optical path and it includes a first optical component 11 and a second optical component 12. The signal processing part performs analysis on the physical features of the light ray received so as to obtain the atmospheric environmental condition and comprises sequentially connected an optical fiber 21, a spectrometer 22, a scanner 23, an optical detector 24 and a computer 25.

The monitor further includes: a position adjustment units which includes an optical support 31, a rotary mechanism and a dynamic device 33. The optical generation part is installed on the optical support 31. The output end of the rotary mechanism is connected and fixed to the optical support 31 so that optical support 31 will rotate. The input end of the rotary mechanism is connected to the output end of the dynamic device 33 so as to provide power to the rotary mechanism. Wherein, the rotary mechanism includes a rotational shaft 321, a bearing 322 and gear transmission mechanism. The gear transmission mechanism includes a driving gear 3231 and a driven gear 3232, and the driven gear 3232 is fixed on the rotational shaft 321 and meshed with the driving gear 3231. The bearing 322 is capped to the rotational shaft 321, and the input end of the rotary mechanism acts as the output end of the rotational shaft 321. The monitor further includes a gearbox 34. The output shaft of the gearbox 34 is connected to the driving gear 3231, and the input end of the gearbox 34 is connected to the output end of the dynamic device 33. The monitor further includes an anemoscope 35 which is connected to the computer 25. The computer 25 is connected to the control end of the dynamic instrument 33, and the dynamic device 33 is motor. The computer 25, through the direction parameters sent from wind direction instrument 35, control the motor to perform the rotational direction and rotational angle of the optical support 31 of position adjustment unit so that the measured values are closer to actual situation.

Figure 2:
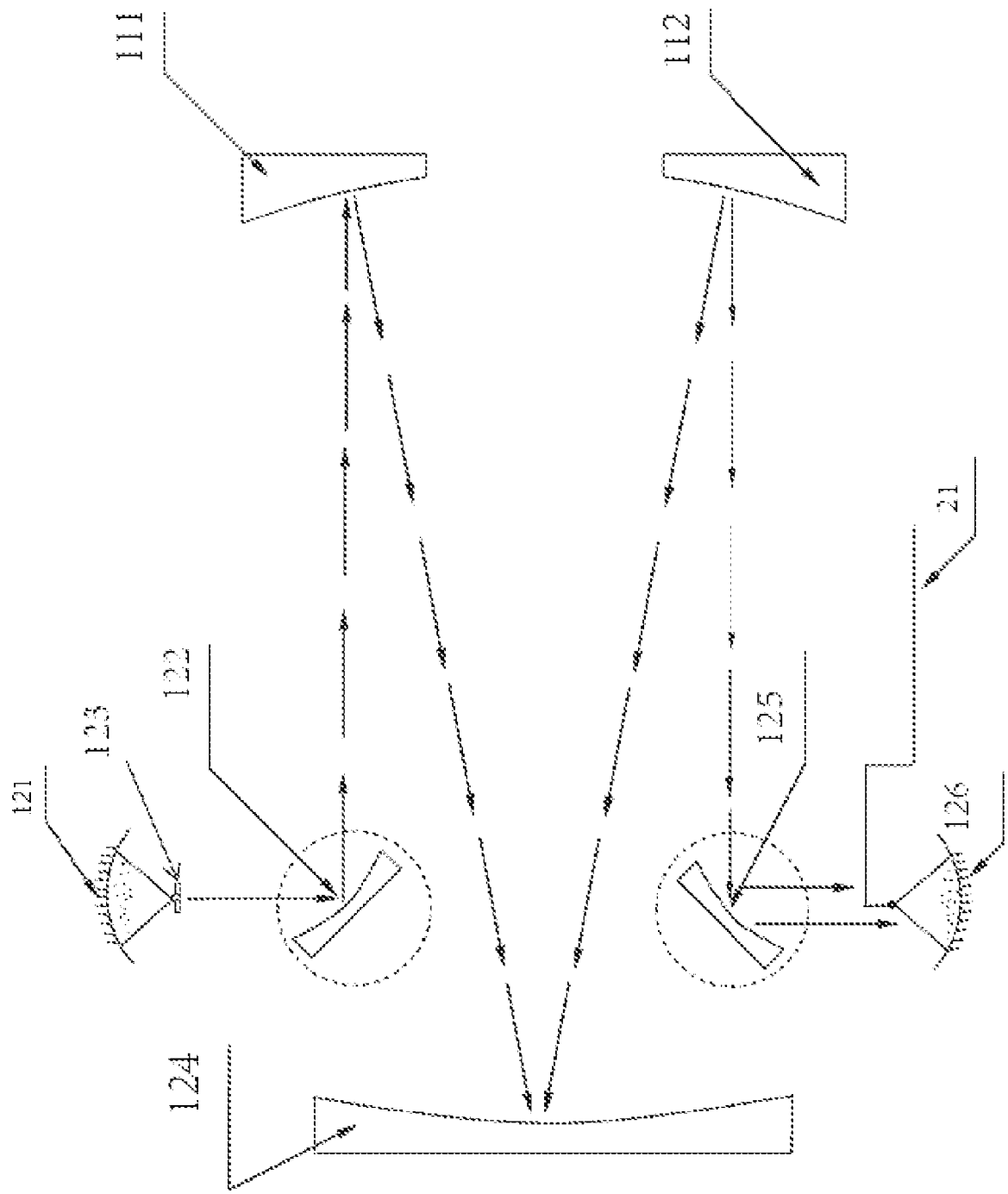
FIG. 2 is a brief structural drawing of the optical generation part of the long optical path gas monitor according to preferred embodiment 1 of the present invention.

In FIG. 2, a brief structural drawing of the optical generation part of the long optical path gas monitor according to preferred embodiment 1 of the present invention is shown. The monitor is open-typed. The optical generation part includes an emitter 121 which emits of ultraviolet light by Xenon lamp, a first planar reflection mirror 122 which is installed on the light ray path emitted by the emitter 121, a first lens 123 which is installed between the emitter 121 and the first planar reflection mirror 122 so as to focus light, a first concave mirror 111 which is installed in the optical path of the light ray reflected by the first planar mirror 122, a second concave mirror 124 which is installed in the optical path of the light ray reflected by the first concave mirror 111, a third concave mirror 112 which is installed in the optical path of the light ray reflected by second concave mirror 124, a fourth concave mirror 125 is installed in the optical path of the light ray reflected by the third concave mirror 112, and a receiver 126 is installed in the optical path of the light ray reflected by the fourth concave mirror 125. Therefore, the light ray is reflected for several times between the first concave mirror 111, the second concave mirror 124 and the third concave mirror 112 so that the optical path of the light ray reaches the needed values (200 meters to 1000 meters), and through the third concave mirror 112, the light ray is reflected to the fourth concave mirror 125, finally, through the fourth concave mirror 125, the light ray is focused onto the receiver 126, above all that, the optical system has completed the mission thereof, and the input end of the optical fiber 21 of the signal processing part 2 is connected to the receiver 126 for further processing. The radius of curvature of the first concave mirror 111, the second concave mirror 124, the third concave mirror 112 and the fourth concave mirror 125 is in the range of 20 cm to 500 cm, and the material of the first planar reflection mirror 122 and all the concave mirrors is silica or ultraviolet optical fused silica of which the reflecting surface coated with Au or Ag and a protection film is also coated. Furthermore, the first optical component 11 is composed of the first concave mirror 111 and the third concave mirror 112, the optical component 12 is composed of emitter 121, the second concave mirror 124, the fourth concave mirror 125 and the receiver 126, the optical component 11 and the second optical component 12 are installed respectively at one of the two ends of the optical support 31, and the distance between the first optical component 11 and the second optical component 12 is from 0.3 meter to 20 meters.

Figure 3:
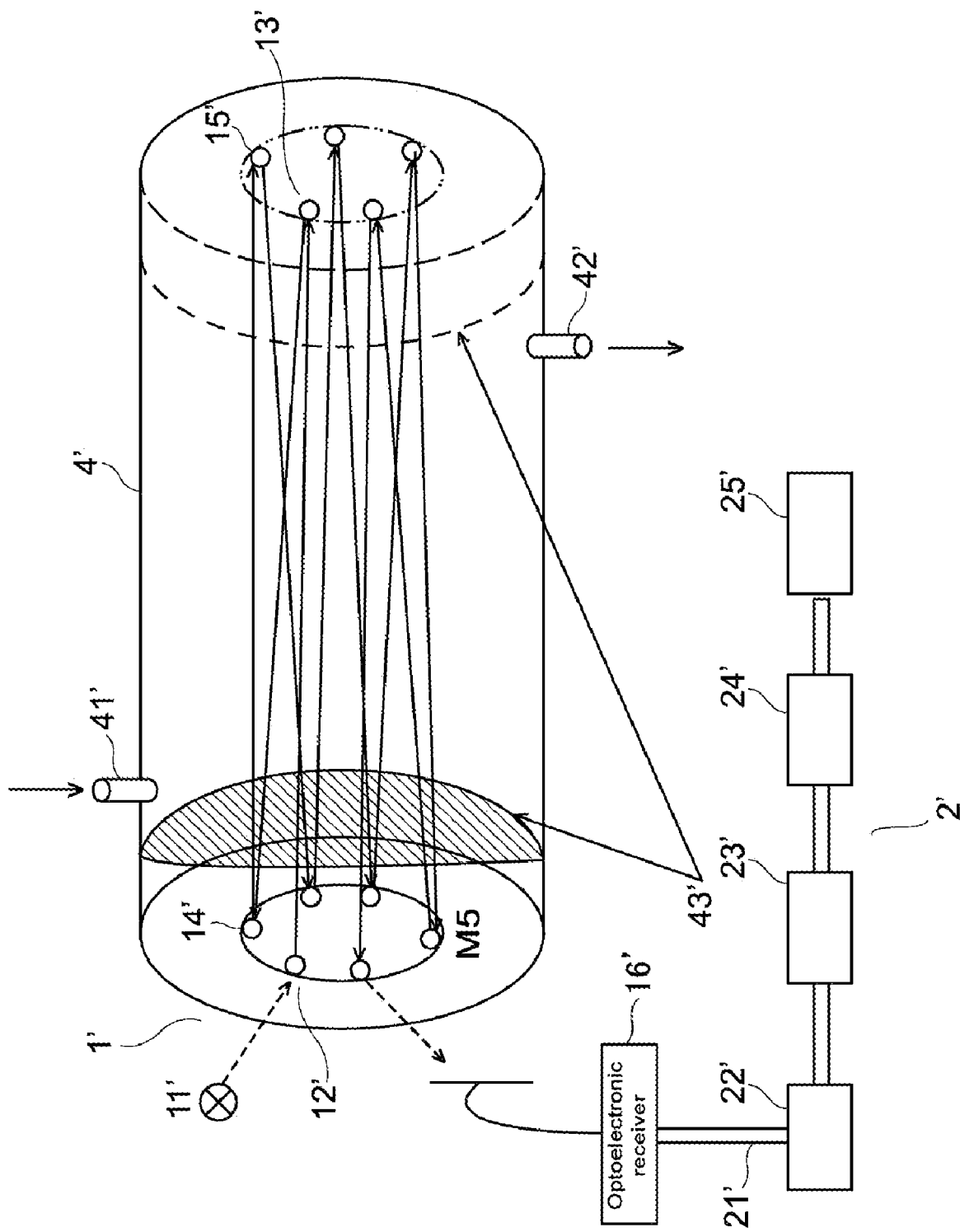
FIG. 3 is a brief structural drawing of the long optical path gas monitor according to preferred embodiment 2 of the present invention.

In FIG. 3, a brief structural drawing of the long optical path gas monitor according to preferred embodiment 2 of the present invention is shown. The monitor is closed-typed and includes optical generation part 1' and signal processing part 2', wherein the optical generation part 1' is installed within a closed body 4'which has an inlet 41'of tested gas and an outlet 42'of tested gas and within which an clean air curtain 43' is installed.

The optical generation part 1' comprises an emitter 11' which is an optical source and is located outside of the closed body 4', a plurality of prisms which are correspondingly installed at the side walls of the closed body 4', wherein, a first prism 12' which receives the light ray emitted by the emitter 11', a second prism 13' which is installed in the optical path of the light ray through the first prism 12', a third prism 14' which is installed in the optical path of light ray totally reflected by the second prism 13', a fourth prism 15' which is installed in the optical path of the light ray totally reflected by the third prism 14', then until a $2k_{th}$ prism which is installed in the optical path of the light ray totally reflected by a $(2k-1)_{th}$ prism, and an optoelectronic receiver 16' which is installed outside of the closed body 4 to receive the light through the $2k_{th}$ prism. The light is reflected back and forth in the plurality of prisms that are set up, and finally, the optical path will reach the required 200 meters to 1000 meters, wherein, k is a natural number and is larger than or equal to 2, moreover, the larger k value is, the shorter the distances among relative prisms is, that is, the closed body 4' has smaller length; here if k is set to be 6, then the number of prisms required is 12, that is, from the first prism 1 to the twelfth prism.

The signal processing part includes an optical fiber 21', a spectrometer 22', a scanner 23', an optoelectronic detector 24' and a computer 25', which are sequentially connected, the input end of the optical fiber 21' being connected to the optoelectronic detector 16'.

The preferred embodiments of the present invention have been disclosed in this specification and the drawings. Even though certain terms have been used, these are used as general meanings to easily transfer and help understand the technology of the present invention and are not intended to limit the scope of the present invention. In addition to the exemplary embodiments disclosed herein, modifications based on the technical spirit of the present invention can be made by a person having ordinary skill in the art to which the present invention pertains.

What is claimed is:

1. A long optical path gas monitor, which is open-typed and includes an optical generation part and a signal processing part, wherein said optical generation part comprising an emitter, a first planar reflection mirror installed in the optical path of the light ray emitted by said emitter, a first concave mirror installed in the optical path of the light ray reflected by said first planar reflection mirror, a second concave mirror installed in the optical path of the light ray reflected by said first concave mirror, a third concave mirror installed in the optical path of the light ray reflected by said second concave mirror, a fourth concave mirror installed in the optical path of the light ray reflected by said third concave mirror, and a receiver installed in the optical path of the light ray reflected by said fourth concave mirror;

the signal processing part comprising sequentially connected an optical fiber, a spectrometer, a scanner, an optoelectronic detector and a computer, the input end of the optical fiber being connected to the receiver; and wherein the long optical path gas monitor further includes a position adjustment unit that comprises an optical support, a rotary mechanism and a dynamic device, said optical generation part is installed on the optical support, and the output end of the rotary mechanism is connected to the optical support to make the optical support rotate, and the input end of the rotary mechanism is connected to the input end of the dynamic device so as to provide power to the rotary mechanism.

2. The long optical path gas monitor as claimed in claim 1, wherein the optical generation part is divided into a first optical component which is composed of said first concave mirror and said third concave mirror, and a second optical component which is composed of said emitter, said second concave mirror, said fourth concave mirror and said receiver, wherein said first optical component and said second optical component are installed respectively at one of the two ends of the optical support, and the distance between said first optical component and said second optical component is in the range of 0.3 meter to 20 meters.

3. The long optical path gas monitor as claimed in claim 1, wherein said rotary mechanism includes a rotational shaft, a bearing and a gear transmission mechanism, wherein said gear transmission mechanism comprises a driving gear and a driven gear fixed on the rotational shaft and meshed with the driving gear, and the bearing is capped to the rotational shaft, and the input end of the rotary mechanism acts as the output end of the rotary shaft.

4. The long optical path gas monitor as claimed in claim 3, further including a gearbox, of which the output shaft being connected to the driving gear and the input end being connected to the output end of the dynamic device.

5. The long optical path gas monitor as claimed in claim 1, further including an anemoscope connected to the computer, the computer is connected to the control end of the dynamic device, and the dynamic device is a motor.

6. The long optical path gas monitor as claimed in claim 1, further including a first lens which is installed between the emitter and the first planar reflection mirror.

7. The long optical path gas monitor as claimed in claim 1, wherein the radius of curvature of the first concave mirror, the second concave mirror, the third concave mirror and the fourth concave mirror is in the range of 20 cm to 500 cm.

8. The long optical path gas monitor as claimed in claim 1, wherein the materials of the first planar reflection mirror and all the concave mirrors is silica or ultraviolet opticalfused silica, the reflecting surface of which is coated with Au or Ag and a protection film is also coated.

9. A long optical path gas monitor, which is close-typed and includes an optical generation part and a signal processing part, wherein the optical generation part is installed within a closed body with an inlet and an outlet of tested gas, the optical generation part comprises: an emitter which is located at the outside of the closed body; a plurality of prisms, which are installed correspondingly on the side walls of the closed body, wherein, a first prism receives the light ray emitted by the emitter, a second prism is set at the optical path through the first prism, a third prism is set at the optical path of total reflection by the second prism, a fourth prism is set at the optical path of total reflection by the third prism, then until a $2k_{th}$ prism is set up at the optical path of total reflection by a $(2k-1)_{th}$ prism; and an optoelectronic receiver is installed outside of the closed body to receive the optical light ray passing through the $2k_{th}$ prism, wherein k is a natural number and is larger than or equal to 2;

the signal processing part includes sequentially connected an optical fiber, a spectrometer, a scanner, an optoelectronic detector and a processor, the input end of the optical fiber being connected to the optoelectronic receiver.

10. The long optical path gas monitor as claimed in claim 7, wherein a clean air curtain is installed in the closed body.

* * * * *